United States Patent [19]
Cacheris et al.

[11] Patent Number: 5,264,204
[45] Date of Patent: Nov. 23, 1993

[54] HYDROPHILIC FREE RADICALS FOR MAGNETIC RESONANCE IMAGING

[75] Inventors: William P. Cacheris, Florissant; T. Jeffrey Dunn, Cedar Hill; Lynn deLearie, University City; Youlin Lin, Ballwin; Jeffrey A. Levine, St. Louis, all of Mo.

[73] Assignee: Mallinckrodt Medical, Inc., St. Louis, Mo.

[21] Appl. No.: 876,548

[22] Filed: Apr. 30, 1992

[51] Int. Cl.$^5$ ............... G01N 24/08; A61K 31/40; A61K 31/415
[52] U.S. Cl. ..................... 424/9; 548/518; 548/542; 548/300.1; 514/422; 514/424; 514/385; 436/173; 128/653.4
[58] Field of Search ............ 424/9, 5; 548/518, 542, 548/300.1; 514/422, 424, 385; 436/173; 128/653.4, 654

[56] References Cited

U.S. PATENT DOCUMENTS

| | | | |
|---|---|---|---|
| 3,502,692 | 3/1970 | Feldman et al. | 260/326.3 |
| 4,834,964 | 5/1989 | Rosen | 424/9 |
| 4,845,090 | 7/1989 | Gries et al. | 514/212 |
| 4,925,652 | 5/1990 | Gries et al. | 424/9 |
| 5,104,641 | 4/1992 | Rosen | 424/9 |

FOREIGN PATENT DOCUMENTS

| | | |
|---|---|---|
| 0236411 | 9/1987 | European Pat. Off. |
| 0375074 | 6/1990 | European Pat. Off. |
| 2225015 | 5/1990 | United Kingdom |
| 8904309 | 5/1989 | World Int. Prop. O. |
| 9000904 | 2/1990 | World Int. Prop. O. |

OTHER PUBLICATIONS

Brasch, RC AJR 141:1019-1023 (1983).
W. R. Couet et al., "Factors Affecting Nitroxide Reduction in Ascorbate Solution and Tissue Homogenates", *Magnetic Resonance Imaging*, vol. 3, pp. 83-88, 1985.

*Primary Examiner*—Glennon H. Hollrah
*Assistant Examiner*—Gary E. Hollinden
*Attorney, Agent, or Firm*—Madson & Metcalf

[57] ABSTRACT

Methods and compositions are disclosed for enhancing magnetic resonance imaging which utilize hydrophilic free radical compounds as magnetic resonance contrast media. Typical magnetic resonance contrast media within the scope of the present invention include stable hydrophilic free radicals having a hydrophilic moiety, such as polyhydroxyalkyl groups and heterocyclic amino-alcohols such as dihydroxypyrrolidine, dihydroxypiperidine, and trihydroxypiperidine, and a stable free radical moiety, such as a nitroxide, phenoxy, or phenoxazinyl free radical moiety.

10 Claims, No Drawings

HYDROPHILIC FREE RADICALS FOR MAGNETIC RESONANCE IMAGING

BACKGROUND OF THE INVENTION

This invention relates to compositions for improving magnetic resonance imaging ("MRI"), magnetic resonance spectroscopy ("MRS"), and magnetic resonance spectroscopy imaging ("MRSI"). More particularly, the present invention relates to hydrophilic free radicals useful as magnetic resonance contrast media.

The technique of MRI encompasses the detection of certain atomic nuclei (those possessing magnetic dipole moments) utilizing magnetic fields and radio-frequency radiation. It is similar in some respects to X-ray computed tomography ("CT") in providing a cross-sectional display of the body organ anatomy with excellent resolution of soft tissue detail. The technique of MRI is advantageously non-invasive as it avoids the use of ionizing radiation.

The hydrogen atom, having a nucleus consisting of a single unpaired proton, has the strongest magnetic dipole moment of any nucleus. Since hydrogen occurs in both water and lipids, it is abundant in the human body. Therefore, MRI is most commonly used to produce images based upon the distribution density of protons and/or the relaxation times of protons in organs and tissues. Other nuclei having a net magnetic dipole moment also exhibit a nuclear magnetic resonance phenomenon which may be used in MRI, MRS, and MRSI applications. Such nuclei include carbon-13 (six protons and seven neutrons), fluorine-19 (9 protons and 10 neutrons), sodium-23 (11 protons and 12 neutrons), and phosphorus-31 (15 protons and 16 neutrons).

While the phenomenon of NMR was discovered in 1945, it is only relatively recently that it has found application as a means of mapping the internal structure of the body as a result of the original suggestion of Lauterbur (*Nature*, 242, 190-191 (1973)). The fundamental lack of any known hazard associated with the level of the magnetic and radio-frequency fields that are employed renders it possible to make repeated scans on vulnerable individuals. Additionally, any scan plane can readily be selected, including transverse, coronal, and sagittal sections.

In an MRI experiment, the nuclei under study in a sample (e.g. protons, $^{19}F$, etc.) are irradiated with the appropriate radio-frequency (RF) energy in a controlled gradient magnetic field. These nuclei, as they relax, subsequently emit RF energy at a sharp resonance frequency. The resonance frequency of the nuclei depends on the applied magnetic field.

According to known principles, nuclei with appropriate spin when placed in an applied magnetic field (B, expressed generally in units of gauss or Tesla ($10^4$ gauss)) align in the direction of the field. In the case of protons, these nuclei precess at a frequency, F, of 42.6 MHz at a field strength of 1 Tesla. At this frequency, an RF pulse of radiation will excite the nuclei and can be considered to tip the net magnetization out of the field direction, the extent of this rotation being determined by the pulse, duration and energy. After the RF pulse, the nuclei "relax" or return to equilibrium with the magnetic field, emitting radiation at the resonant frequency. The decay of the emitted radiation is characterized by two relaxation times, $T_1$ and $T_2$. $T_1$ is the spin-lattice relaxation time or longitudinal relaxation time, that is, the time taken by the nuclei to return to equilibrium along the direction of the externally applied magnetic field. $T_2$ is the spin-spin relaxation time associated with the dephasing of the initially coherent precession of individual proton spins. These relaxation times have been established for various fluids, organs, and tissues in different species of mammals.

For protons and other suitable nuclei, the relaxation times $T_1$ and $T_2$ are influenced by the environment of the nuclei (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain molecules or other nuclei which are paramagnetic. Chemical compounds incorporating these paramagnetic molecules or nuclei may substantially alter the $T_1$ and $T_2$ values for nearby nuclei having a magnetic dipole moment. The extent of the paramagnetic effect of the given chemical compound is a function of the environment within which it finds itself.

In MRI, scanning planes and sliced thicknesses can be selected. This selection permits high quality transverse, coronal and sagittal images to be obtained directly. The absence of any moving parts in MRI equipment promotes a high reliability. It is believed that MRI has a greater potential than CT for the selective examination of tissue characteristics. The reason for this being that in CT, X-ray attenuation and coefficients alone determine image contrast, whereas at least four separate variables ($T_1$, $T_2$, proton density, and flow) may contribute to the MRI signal. For example, it has been shown (Damadian, *Science*, 171, 1151 (1971)) that the values of the $T_1$ and $T_2$ relaxation in tissues are generally longer by about a factor of two (2) in excised specimens of neoplastic tissue compared with the host tissue.

By reason of its sensitivity to subtle physiochemical differences between organs and/or tissues, it is believed that MRI may be capable of differentiating different tissue types and in detecting diseases which induce physicochemical changes that may not be detected by X-ray or CT which are only sensitive to differences in the electron density of tissue.

Although most prior art efforts to develop MRCM are based upon paramagnetic metal complexes, some work has been done with nitroxide radicals as MRCM. For example, U.S. Pat. No. 4,834,964 to Rosen discloses charged organic nitroxides as MRCM for cerebrospinal fluid. U.S. Pat. Nos. 4,845,090 and 4,925,652 to Gries et al. disclose a class of nitroxyl compounds for enhancing NMR imaging. Free radicals are inherently less potent than metal ion complexes for proton MRI because a simple free radical compound has only one unpaired electron compared to several for paramagnetic metal ions. For instance, gadolinium(III) has seven unpaired electrons. In addition, nitroxide free radicals tend to quickly reduce and therefore, lack sufficient in vivo stability. (Couet, W., et al., *Magnetic Resonance Imaging*, Vol. 3, pp. 83-88 (1985)). Also, known nitroxide free radicals tend to be hydrophobic and are not sufficiently water soluble to be effective MRCM.

From the foregoing, it would be a significant advancement in the art to provide stable hydrophilic free radicals as MRCM having proton relaxivities comparable to that of paramagnetic metal ions.

Such MRCM are disclosed and claimed herein.

SUMMARY OF THE INVENTION

The present invention provides methods and compositions for improved magnetic resonance imaging and spectroscopy, utilizing stable hydrophilic free radicals, such as nitroxide, phenoxy, and phenoxazinyl free radicals. One class of stable, hydrophilic free radicals within the scope of the present invention include known hydrophilic core molecules, such as non-ionic XRCM, having one or more stable free radicals substituted thereon. Hydrophilic core molecules are preferably water rich, organic species which has its own large sphere of hydration. Such a species, modified to include one or more stable free radical components in close proximity to the hydration sphere, may display enhanced proton relaxivity due to the magnetic interactions between nearby ion radicals and the solubilizing water molecules. The following tri-substituted benzene-based compounds illustrate this class of compounds:

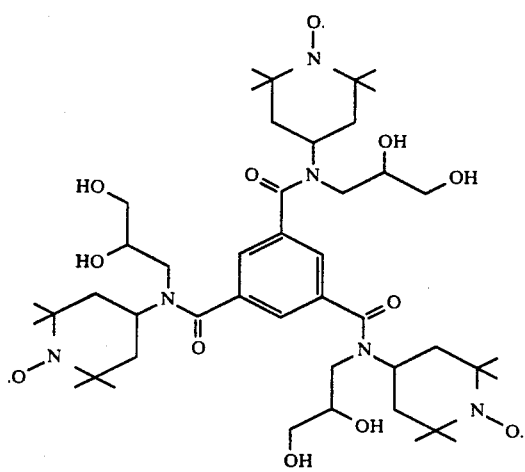

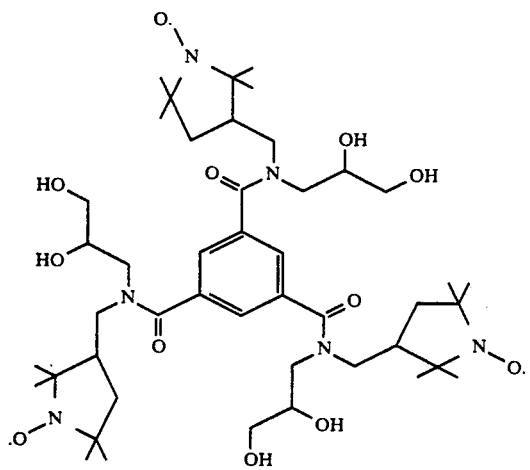

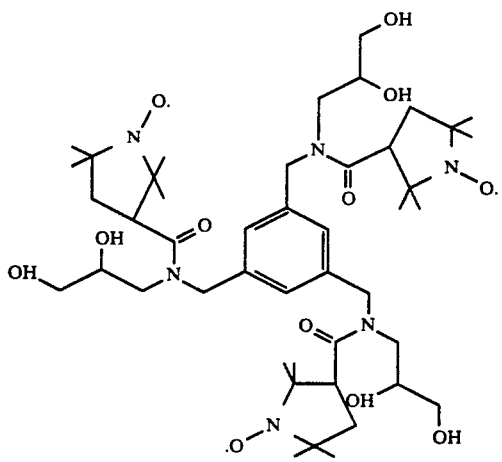

Alternatively, stable hydrophilic free radicals are prepared by adding hydrophilic substituents to stable free radicals. Examples of such compounds include tame-based compounds, pyrrolidine-mononitroxyl structures, and dinitroxyls of vicinal diamines. The following are typical tame based compounds within the scope of the present invention:

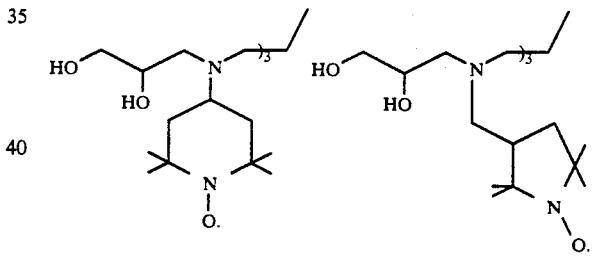

The following are typical pyrrolidine-mononitroxyl compounds within the scope of the present invention:

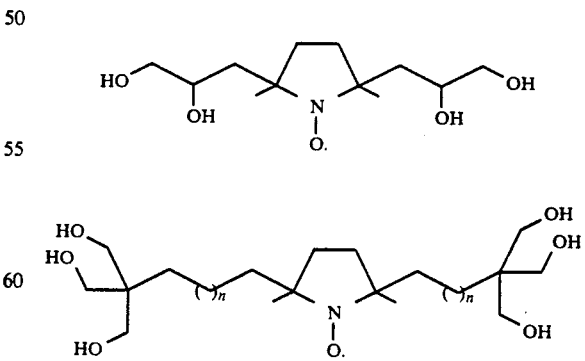

Where n is from 0 to 3. The following general structure illustrates typical dinitroxyls of vicinal diamines within the scope of the present invention:

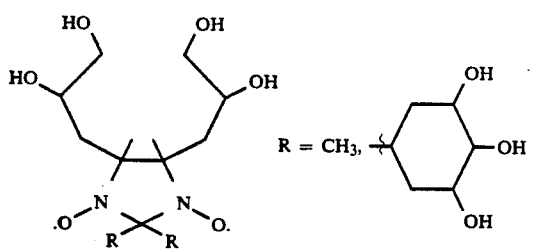

Also disclosed are diagnostic compositions and methods of performing MR diagnostic procedures which involve administering to a warm-blooded animal a diagnostically effective amount of the above-described hydrophilic free radical MRCM compositions and then exposing the warm-blooded animal to a MR procedure.

DETAILED DESCRIPTION OF THE INVENTION

The present invention provides novel hydrophilic free radical MRCM. The MRCM of the present invention are prepared either by placing stable free radicals, such as nitroxide, phenoxy, and phenoxazinyl free radicals, on hydrophile core molecules or by incorporating hydrophilic substituents on the free radical itself. Thus, the MRCM within the scope of the present invention comprise a stable free radical moiety and a hydrophilic moiety.

As used herein, stable free radicals include physiologically compatible free radicals which resist reduction under reducing conditions, such as those encountered in vivo. It is believed the presence of hydrophilic moieties promotes free radical stability.

As used herein, the term nitroxide free radical includes physiologically stable compounds having the general structure $R_5R_6N-O.$; wherein $R_5$ and $R_6$ may be alkyl, hydroxyalkyl, alkoxyalkyl, and wherein $R_5$ and $R_6$ may optionally be joined together to form a 5 to 7 member heterocyclic ring with the nitroxide nitrogen atom. Examples of some possible stable nitroxide radicals which may be used within the scope of the present invention are described in U.S. Pat. No. 4,925,652 to Gries et al. and in EP 0 375 074 to Hafslund Nycomed Innovation AB, which are hereby incorporated by reference.

As used herein, the term phenoxy free radical includes physiologically stable compounds having the following general structure:

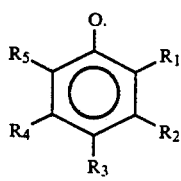

where one or more of the substituents $R_1$, $R_2$, $R_3$, $R_4$, and $R_5$ is hydrophilic.

As used herein, the term phenoxazinyl free radical includes physiologically stable compounds having the following general structure:

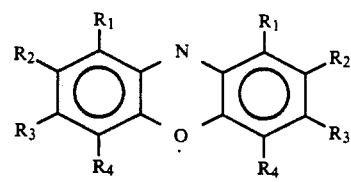

where one or more of the substituents $R_1$, $R_2$, $R_3$, and $R_4$ is hydrophilic.

Hydrophilic moieties used within the scope of the present invention include hydrophilic "cores" such hydrophilic tri-substituted benzene-based compounds used with non-ionic XRCM. As used herein, hydrophilic moieties and hydrophilic cores include molecules with a high affinity for water such that log p<0, where p is the partition coefficient between octanol and water (the molecule's concentration in the octanol phase divided by the molecule's concentration in the water phase). Such species have a large sphere of hydration capable of being placed in close proximity to the free radical group.

Typical hydrophilic moieties within the scope of the present invention include polyhydroxyalkyl groups and heterocyclic amino-alcohols such as dihydroxypyrrolidine, dihydroxypiperidine, and trihydroxypiperidine (1-4) below:

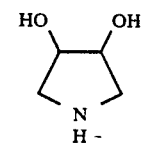

1

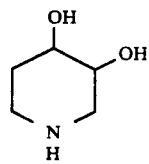

2

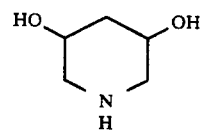

3

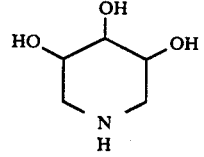

4

Trans-3,4-pyrrolidinediol may be prepared in high yield from tartaric acid as described by Nagel, U. Angew., *Int. Ed. Engl.*, Vol. 23(6), p. 435 (1984), which is incorporated herein by reference.

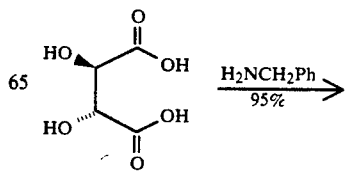

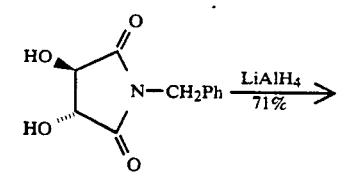

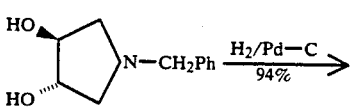

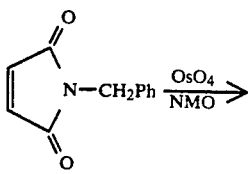

Cis-3,4-pyrrolidinediol may be prepared in low yield via a Diels-Alder route as described by Defoin, Pires, and Streith, *Synlett*, Vol. 2, p. 111 (1990), which is incorporated herein by reference.

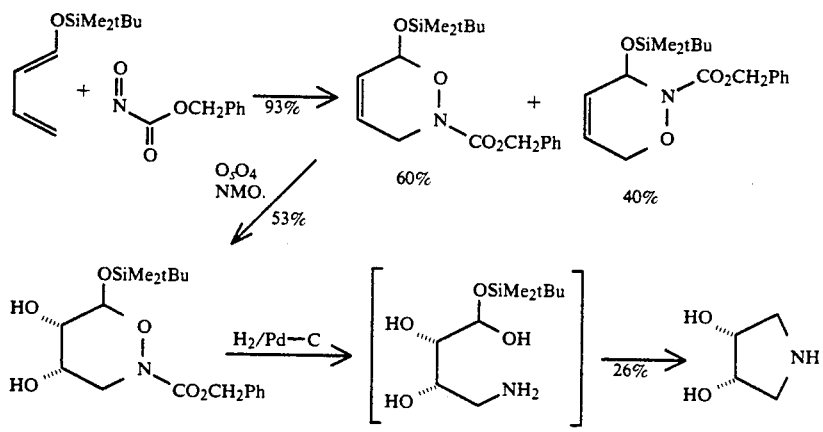

.NMO = N-Methylmorpholine-N-oxide

A better route for preparing cis-3,4-pyrrolidinediol might be from N-benzylmaleimide, in a fashion similar to that used for the trans compound.

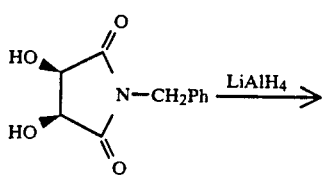

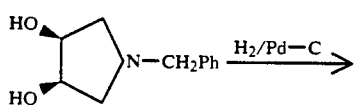

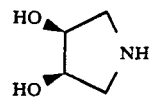

Various stereoisomers of 3,4,5-piperidinetriol may be prepared, either from 1,2-dihydropyridine, as described by Backenstrass and Tschamber, *Tetrahedron Lett.*, Vol. 31(5), p. 2139 (1990), which is incorporated by reference, or from pyranose sugars as described by Bernotos, Papndrou, Urbach, and Ganem, *Tetrahedron Lett.*, Vol. 31(24), p. 3393 (1990), which is incorporated by reference.

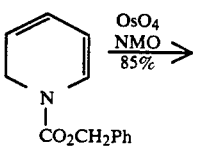

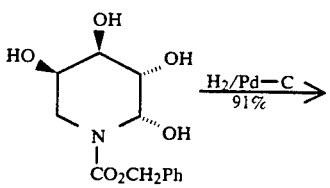

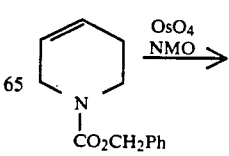

CiB-3,4-piperidinediol may be prepared from 1,2,3,5-tetrahydropyridine in a fashion similar to 3,4,5-piperidinetriol above.

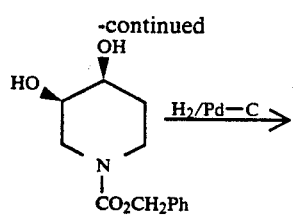

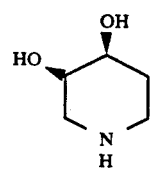

Trans-3,4-piperidinediol may be prepared in a similar fashion via a trans-hydroxylation.

3,5-piperidinediol may be prepared by cyclo-amination of 1,2:4,5-diepoxypentane. Similar reactions have been reported by Stetter and Zoller, *Chem. Ber.*, Vol. 98(5), p. 1446 (1965) in CA63:4299c and by Paul and Tchelitcheff, *Compt. rend.*, Vol. 225, p. 1334 (1947) in CA42:2604h, which are incorporated herein by reference.

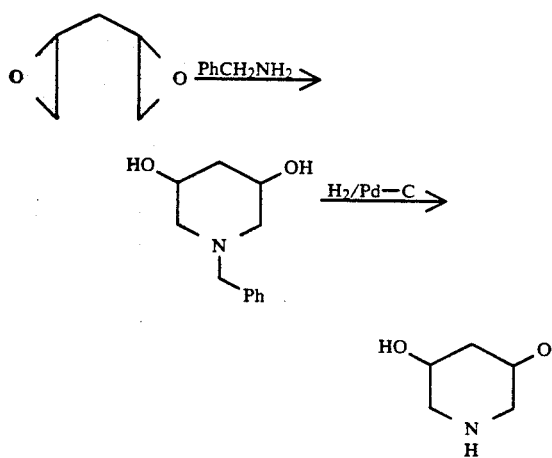

The hydrophilic free radical MRCM compounds of this invention are preferably formulated into diagnostic compositions for enteral or parenteral administration. The MRCM formulations may contain conventional pharmaceutical carriers and excipients appropriate for the type of administration contemplated.

For example, parenteral formulations for proton imaging advantageously contain a sterile aqueous solution or suspension of a hydrophilic free radical MRCM according to this invention. Various techniques for preparing suitable pharmaceutical solutions and suspensions are known in the art. Such solutions also may contain pharmaceutically acceptable buffers, stabilizers, antioxidants, and electrolytes, such as sodium chloride. Parenteral compositions may be injected directly or mixed with a large volume parenteral composition for systemic administration.

Formulations for enteral administration may vary widely, as is well-known in the art. In general, such formulations include a diagnostically effective amount of a hydrophilic free radical MRCM in an aqueous solution or suspension. Such enteral compositions may optionally include buffers, surfactants, adjuvants, thixotropic agents, and the like. Compositions for oral administration may also contain flavoring agents and other ingredients for enhancing their organoleptic qualities.

The diagnostic compositions within the scope of the present invention are administered in doses effective to achieve the desired enhancement of the NMR image. Such doses may vary widely, depending upon the number of free radical moieties, the organs or tissues which are the subject of the imaging procedure, the NMR imaging equipment being used, etc. Typical doses of the diagnostic compositions are in the range from about 0.001 to about 20 mmol/kg body weight, and preferably less than 5 mmol/kg body weight.

The diagnostic compositions of this invention are used in a conventional manner in magnetic resonance procedures. Compositions may be administered in a sufficient amount to provide adequate visualization, to a warm-blooded animal either systemically or locally to an organ or tissues to be imaged, and the animal then subjected to the MRI procedure. The compositions enhance the magnetic resonance images obtained by these procedures.

The following examples are offered to further illustrate the present invention. These examples are intended to be purely exemplary and should not be viewed as a limitation on any claimed embodiment.

EXAMPLE 1

Synthesis of 2,5-(2,3-dihydroxypropyl)-2,5-dimethylpyrrolidine-1-oxyl

To a solution of nitroethane (85.5 g, 81.8 mL, 1.14 mol) in 450 mL of methanol was added a solution of 25% sodium methoxide (51.2 g, 207 mL, 0.95 mol). To the resulting mixture was added dropwise methyl vinyl ketone (63.3 g, 75.1 mL, 0.90 mol). After stirring for 2 hours, glacial acetic acid (94.4 g, 90 mL, 1.57 mol) was added and the solvents were removed under reduced pressure. The residue was partitioned between dichloromethane and water (300 mL each) and the layers were separated. The organic layer was washed three times with 200 mL of 10% sodium carbonate solution followed by 200 mL of saturated sodium chloride solution. The solvent was evaporated and the residue was distilled to give nitroketone 1 (83.1 g, 0.57 mol, 50%). Boiling point 60°-63° C., 0.5 mm.

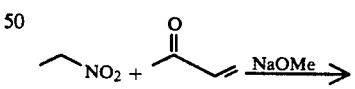

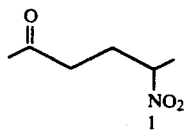

Portions of zinc dust (108.3 g, 1.66 mol) were added to a mechanically-stirred mixture of 1 (60.2 g, 0.42 mol) and ammonium chloride (22.2 g, 0.42 mol) in 345 mL of water cooled to 10° C. After the addition was complete, the mixture was stirred an additional 30 minutes and then filtered, washing the cake well with methanol (400 mL). The filtrate was evaporated to 100 mL volume, saturated with borax and extracted three times with dichloromethane (300 mL). The combined organic extracts were dried over anhydrous potassium carbonate and evaporated. The residue was distilled to give nitrone 2 (9.6 g, 0.08 mol, 19%). Boiling point 62°–65° C., 0.5 mm.

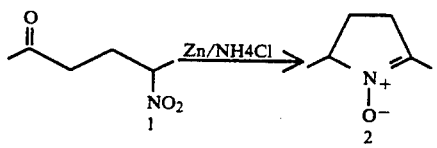

To nitrone 2 (20.3 g, 0.18 mol) in 100 mL anhydrous tetrahydrofuran at −10° C. under argon atmosphere was added dropwise a 2M solution of methyl magnesium chloride (100 mL, 0.20 mol) in tetrahydrofuran. After the addition was complete, the reaction mixture was allowed to reach 25° C. and stirred for 20 hours. The reaction was cooled to 0° C. and saturated ammonium chloride solution (35 mL) was added to precipitate inorganic salts. The tetrahydrofuran solution was decanted, the residue was washed with additional tetrahydrofuran, and the combined extracts were evaporated to give an oil. The crude oil was dissolved in methanol (210 mL) and concentrated ammonium hydroxide (22.3 mL) and stirred with cupric acetate (3.2 g, 0.01mol). Air was bubbled through the solution until a dark blue color persisted. The methanol was removed under reduced pressure and the remaining aqueous solution was extracted several times with dichloromethane. The combined organic solutions were washed successively with 100 mL each of saturated sodium carbonate and saturated sodium chloride, dried over anhydrous potassium carbonate and evaporated to give nitrone 3 (27.5 g, 0.18 mol, 100%) which was used without further purification.

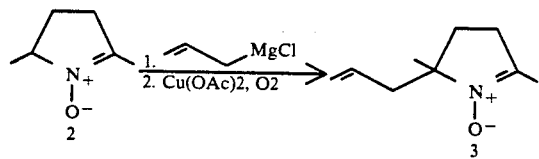

Crude 3 (19.2 g, 0.13 mol) was dissolved in 110 mL of anhydrous tetrahydrofuran and cooled to −10° C. under argon atmosphere. Then a 2M solution of methyl magnesium chloride (95 mL, 0.19 mol) in tetrahydrofuran was added dropwise. The solution was allowed to slowly reach 25° C and stirred for 20 hrs. The same workup procedure outlined for 3 was followed to give the desired nitroxide 4 as a crude gum. Further purification of 4 was achieved via Kugelrohr distillation to give pure diallyl nitroxide 4 (11.4 g, 0.06 mol, 45%); collected fractions from 45°–60° C., 1 mm.

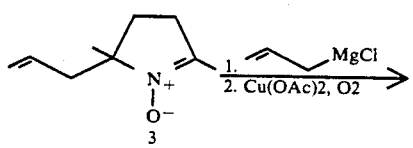

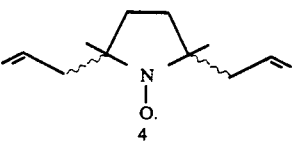

Purified diallyl nitroxide 4 (5 g, 0.026 mol) was dissolved in 150 mL of acetone and N-methyl-morpholine oxide (11.2 g, 0.096 mol) was added as a solid powder. The slurry was cooled to 0° C. under argon atmosphere and a solution of osmium tetroxide (16.5 mL of a 2 mg/mL solution, 0.13 mmol) was added dropwise at a moderate rate. The mixture was stirred at 0° C. for 1 hr., then at 10° C. for 20 hrs. The reaction solution was poured over silica gel (20 g) and the solvents were allowed to evaporate in the hood until the mixture was a dry powder. This powder was placed on top of a column of silica gel (100 g) and a methanol/dichloromethane solvent gradient was eluted through the column. Further purification was necessary; this material (5.6 g) was passed through reversed phase packing (YMC-ODS) with a water/methanol gradient as eluant. The pure fractions were combined to give tetrahydroxy nitroxide 5 (1.4 g, 0.005 mol, 19%) as a viscous yellow gum.

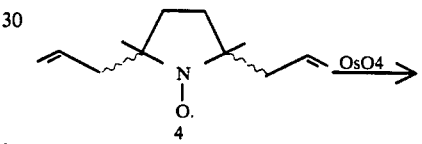

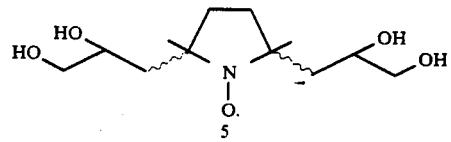

HPLC chromatography purity (3.5% acetonitrile, 25 mM ammonium phosphate, pH 6.0) tetrahydroxy nitroxide 5 was 99.3%. Analytical calculated for $C_{12}H_{24}NO_5$: C, 54.94; H, 9.22; N, 5.34. Found: C, 54.48; H, 9.29; N, 5.13. The $T_1$ relaxivity ($R_1$) was measured to be 0.27 mmol$^{-1}$sec$^{-1}$ at 20 MHz.

2 mL of rat blood were mixed with 2 mL of 100 mM solution of tetrahydroxy nitroxide 5 to give a final concentration of 5 to 50 mM in diluted rat blood. The $T_1$ relaxivity ($R_1$) was measured to be approximately the same as the relaxivity in water. The $T_1$ was measured over time and remained constant over 15 hours.

EXAMPLE 2

Synthesis of 3-[1,3,5-(benzyl-2,3-dihydroxypropyl)]carboxyamido-2,2,5,5-tetramethylpyrrolidine-1-oxyl To a solution of allyl amine (26.8 g, 35.2 mL, 0.470 mol) in methanol (30 mL) cooled in an ice bath was added 5N hydrochloric acid (31 mL, 0.155 mol). Then 1,3,5-tribenzaldehyde (5.0 g, 0.031 mol) was added as a solid powder. To the resulting solution was added sodium cyanoborohydride (29.6 g, 0.47 mol) in portions over 30 min. The mixture was stirred at 25° C. for 20 hours. Concentrated hydrochloric acid was added to the ice-cooled reaction mixture until the pH reached 4.

The solvents were removed under pressure and water was added to dissolve the solids. The pH was brought to 10 with 6N potassium hydroxide and the solution was extracted several times with dichloromethane. The combined organic layers were washed with saturated sodium chloride, dried over anhydrous sodium sulfate and evaporated under reduced pressure to give crude triamine 6. Further purification of 6 was achieved via chromatography over silica gel using a methanol/dichloromethane gradient as eluent. Pure fractions were combined to give triamine 6 as a clear colorless oil (6.2 g, 0.022 mol, 70%).

A slurry of triamide 8 (2.0 g, 0.003 mol) and N-methylmorpholine oxide (1.9 g, 0.017 mol) in 50 mL of acetone was cooled to 0° C. under argon atmosphere. Then a solution of osmium tetroxide (1.9 mL of a 2 mg/mL solution in water, 0.015 mmol) was added dropwise. The mixture was stirred at 0° C. for 1 hour, then at 25° C. for 20 hours. The reaction mixture was poured over silica gel (10 g) and the solvents were evaporated until the mixture was powdery. This material was loaded onto a column of silica gel (100 g) and eluted with a methanol/dichloromethane gradient to obtain pure nitroxide 9 (2.0 g, 0.002 mol, 80%). NMR data were consistent with the assigned structure.

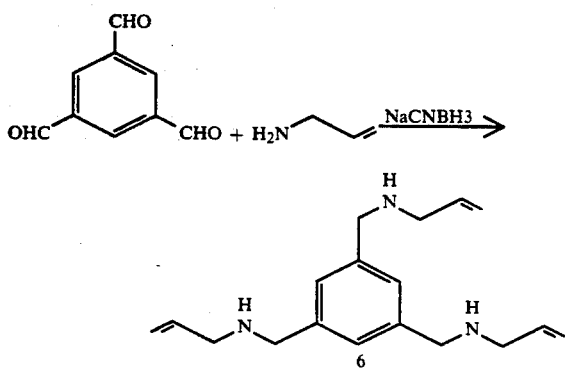

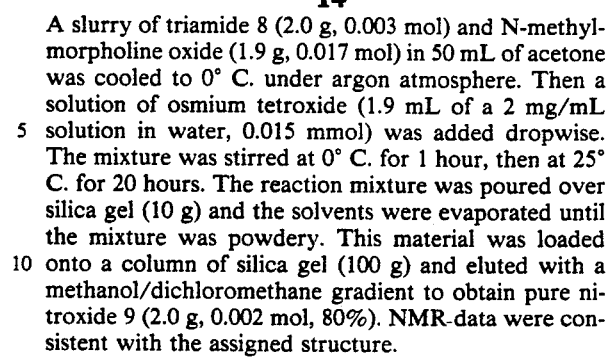

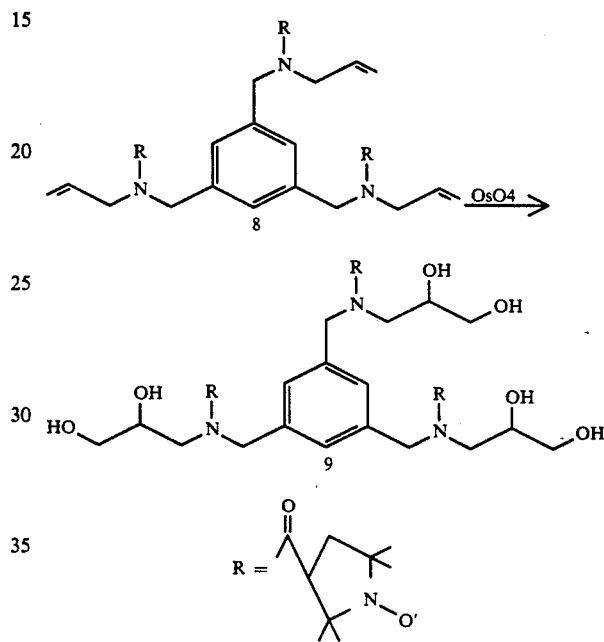

A mixture of triamine 6 (5.0 g, 0.018 mol) and the N-hydroxysuccinimide active ester of 3-carboxy-2,2,5,5-tetramethylpyrollidine-1-oxyl, 7 (5.1 g, 0.018 mol), in N,N-dimethylacetamide (30 mL) was heated in an oil bath at 80° C. for 20 hours. The solvent was removed under reduced pressure and the residue was partitioned between water and dichloromethane. The layers were separated and the organic solution was dried over anhydrous sodium sulfate and evaporated under reduced pressure to give crude triamide 8. The gum was further purified via silica gel chromatography using a methanol/dichloromethane gradient as eluant.to give pure 8 (9.9 g, 0.13 mol, 70%). NMR data were consistent with the assigned structure.

From the foregoing, it will be appreciated that the present invention provides stable hydrophilic free radicals as MRCM.

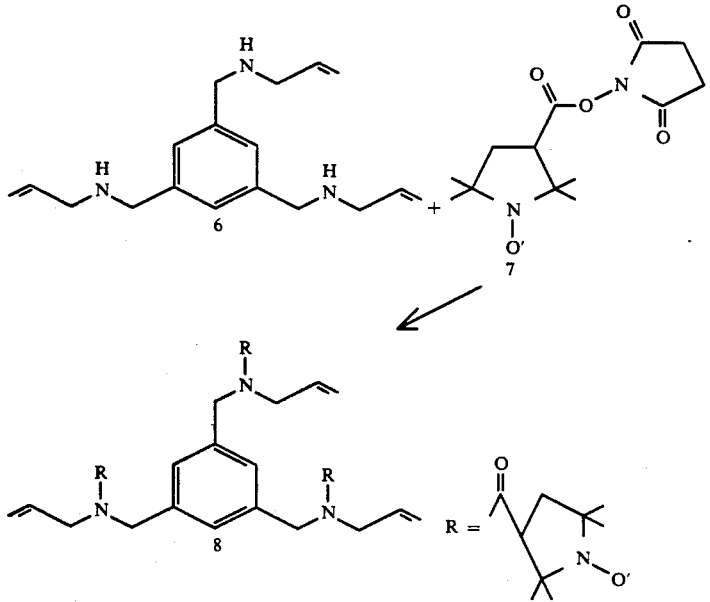

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for obtaining magnetic resonance images of body organs and tissues which comprises:
   (a) administering to a mammal, a diagnostically effective amount of a stable hydrophilic free radical in a pharmaceutically acceptable carrier, said stable hydrophilic free radical having the following general formula:

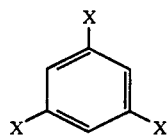

where X is selected from

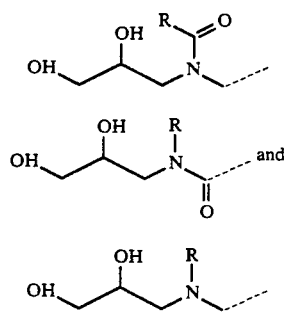

where R is a stable nitroxide; and
   (b) imaging the organs and tissues.

2. A method for obtaining magnetic resonance images as defined in claim 1, wherein R has the following structure:

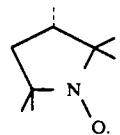

3. A method for obtaining magnetic resonance images as defined in claim 1, wherein R has the following structure:

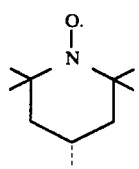

4. A method for obtaining magnetic resonance images as defined in claim 1, wherein R has the following structure:

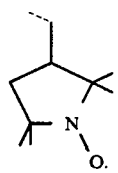

5. A diagnostic composition suitable for enteral or parenteral administration to a warm-blooded animal comprising:

a diagnostically effective amount of a stable hydrophilic free radical containing a hydrophilic moiety and a stable nitroxide moiety, said stable hydrophilic free radical having the following general formula:

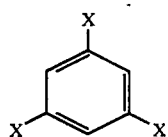

where X is selected from

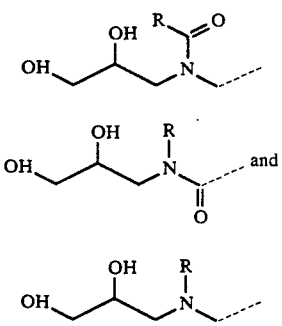

where R is the stable nitroxide moiety; and
a pharmaceutically acceptable carrier.

6. A diagnostic composition as defined in claim 5, wherein R has the following structure:

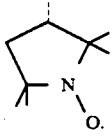

7. A diagnostic composition as defined in claim 5, wherein R has the following structure:

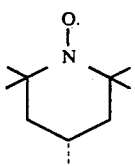

8. A diagnostic composition as defined in claim 5, wherein R has the following structure:

9. A method for obtaining magnetic resonance images of body organs and tissues which comprises:

(a) administering to a mammal, a diagnostically effective amount of a stable hydrophilic free radical in a pharmaceutically acceptable carrier, wherein the stable hydrophilic free radical administered to the mammal has the following general formula:

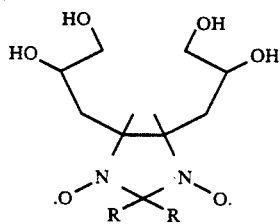

where R is selected from the group consisting of CH₃ or the following substituent:

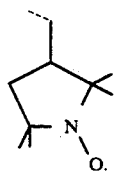

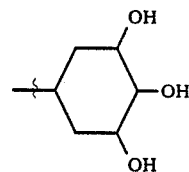

and;

(b) imaging the organs and tissues.

10. A diagnostic composition suitable for enteral or parenteral administration to a warm-blooded animal comprising:

a diagnostically effective amount of a stable hydrophilic free radical containing a hydrophilic moiety and a stable free radical moiety, wherein the stable hydrophilic free radical has the following general formula:

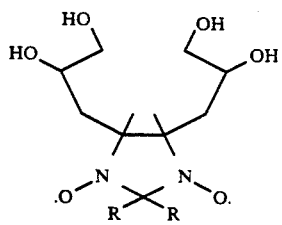

where R is selected from the group consisting of CH₃ or the following substituent:

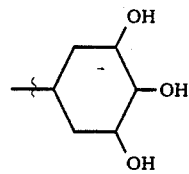

and
a pharmaceutically acceptable carrier.

* * * * *